(12) United States Patent
Szapiro et al.

(10) Patent No.: US 11,027,074 B2
(45) Date of Patent: Jun. 8, 2021

(54) ELASTIC AND SLIDING VALVULAR JOINT, SUITABLE TO WORK IN PRE-FILLED SYRINGES AND SAID SYRINGES

(71) Applicants: Germán Andrés Szapiro, Ciudad de Buenos Aires (AR); Saúl Moreno Bonino, Moreno (AR); Jaime Luis Szapiro, Ciudad de Buenos Aires (AR)

(72) Inventors: Germán Andrés Szapiro, Ciudad de Buenos Aires (AR); Saúl Moreno Bonino, Moreno (AR); Jaime Luis Szapiro, Ciudad de Buenos Aires (AR)

( * ) Notice: Subject to any disclaimer, the term of this patent is extended or adjusted under 35 U.S.C. 154(b) by 303 days.

(21) Appl. No.: 15/916,319

(22) Filed: Mar. 9, 2018

(65) Prior Publication Data

US 2019/0117901 A1 Apr. 25, 2019

(30) Foreign Application Priority Data

Oct. 19, 2017 (AR) .............................. 20170102902

(51) Int. Cl.
*A61M 5/315* (2006.01)
*A61M 5/19* (2006.01)
*A61M 5/31* (2006.01)

(52) U.S. Cl.
CPC .......... *A61M 5/31596* (2013.01); *A61M 5/19* (2013.01); *A61M 5/31505* (2013.01);
(Continued)

(58) Field of Classification Search
CPC .... A61M 5/31596; A61M 5/19; A61M 5/284; A61M 2005/3106; A61M 2005/3128;
(Continued)

(56) References Cited

U.S. PATENT DOCUMENTS

| 3,570,486 A | * | 3/1971 | Engelsher | ........... | A61M 5/2429 |
| | | | | | 604/88 |
| 4,464,174 A | * | 8/1984 | Ennis | .................... | A61M 5/284 |
| | | | | | 604/236 |

(Continued)

FOREIGN PATENT DOCUMENTS

| AR | 026723 B1 | 2/2003 |
| AR | 082099 B1 | 11/2012 |
| CN | 102861369 A | * 1/2013 |

OTHER PUBLICATIONS

English Translation of CN 102861369A.*
English abstract of AR 026723 B1.
English abstract of AR 082099 B1.

*Primary Examiner* — Tiffany Legette
*Assistant Examiner* — Alexandra LaLonde
(74) *Attorney, Agent, or Firm* — Ladas & Parry LLP

(57) ABSTRACT

An elastic and sliding valvular joint for pre-filled syringes, which comprises a single chamber with an injectable product or two chambers that contain isolated products to be mixed before the injection is described. The valvular joint acts as a temporary closure, which prevents the internal chamber from communicating with the outside, or between both internal chambers. The joint comprises two discoid cooperative elements arranged on the syringe and with its edge against the internal surface: an elastic discoid plug and a sliding receiving discoid seat. The receiving discoid seat includes a central passage tube facing the hollow cylinder, and the elastic base of the plug fits in a removable manner inside a cylindrical cavity of the opening of the central passage tube of the seat.

18 Claims, 6 Drawing Sheets

(52) U.S. Cl.
CPC ............... *A61M 5/31511* (2013.01); *A61M 2005/3106* (2013.01); *A61M 2005/3128* (2013.01); *A61M 2205/0216* (2013.01)

(58) Field of Classification Search
CPC ............ A61M 5/31505; A61M 5/2066; A61M 2005/287; A61M 2205/0216; A61J 1/2093
See application file for complete search history.

(56) References Cited

U.S. PATENT DOCUMENTS

| | | | | |
|---|---|---|---|---|
| 6,149,628 | A | * | 11/2000 | Szapiro ............. A61M 5/31596 604/191 |
| 6,602,223 | B2 | * | 8/2003 | Szapiro ................ A61M 5/284 604/89 |

* cited by examiner

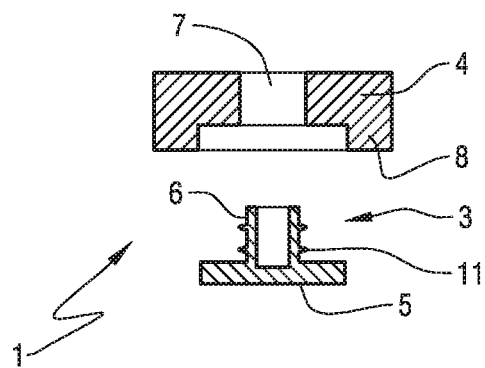
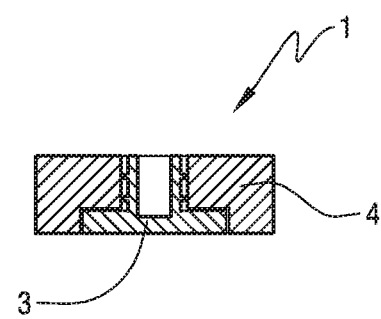
Fig. 1  Fig. 2
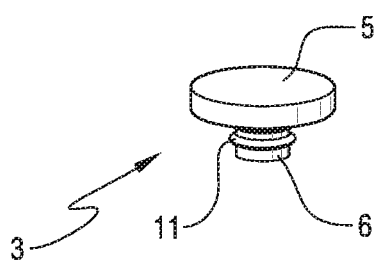
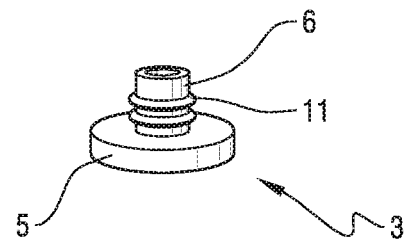
Fig. 3  Fig. 4
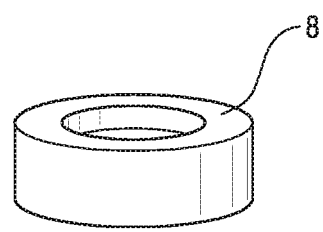
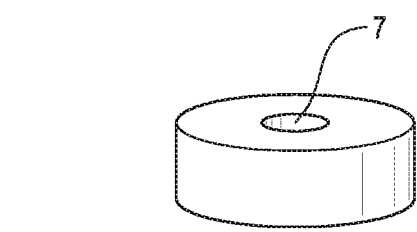
Fig. 5  Fig. 6

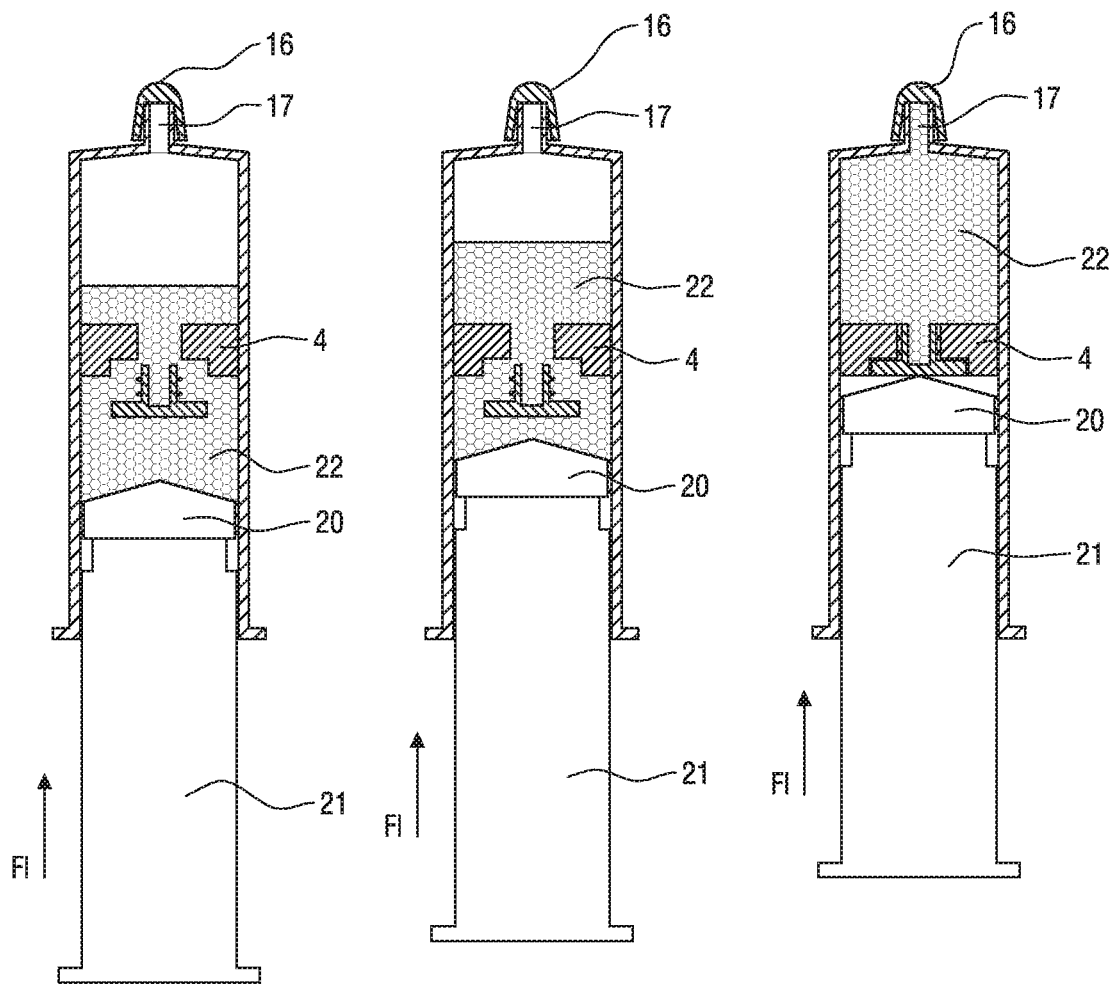

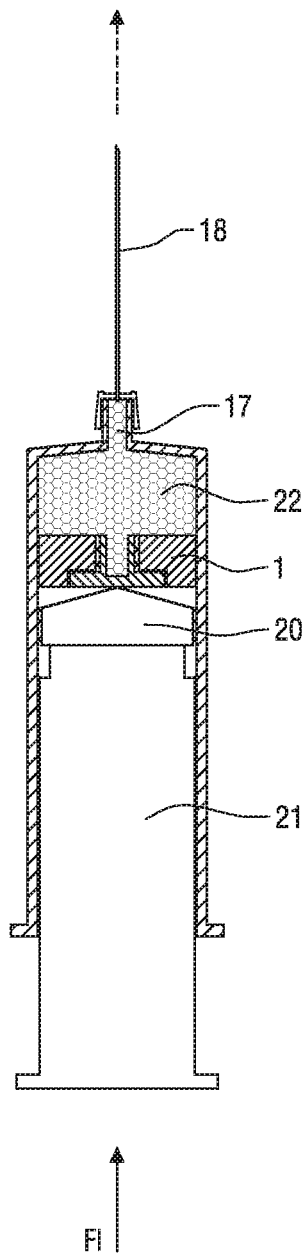
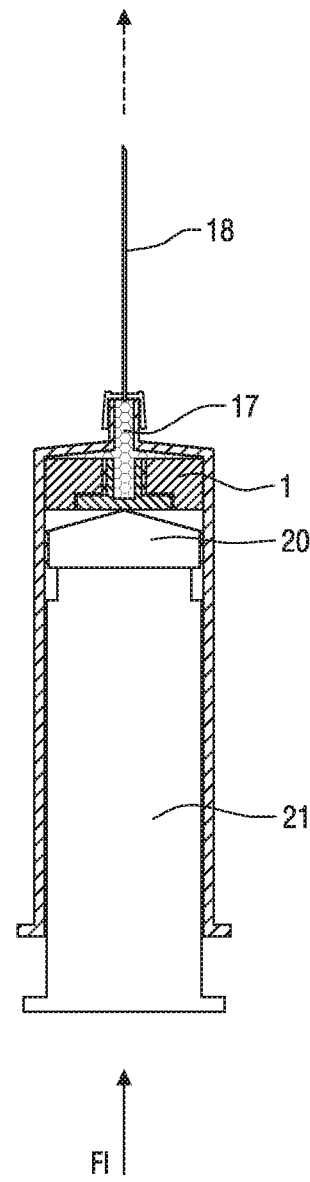
Fig. 14
Fig. 15

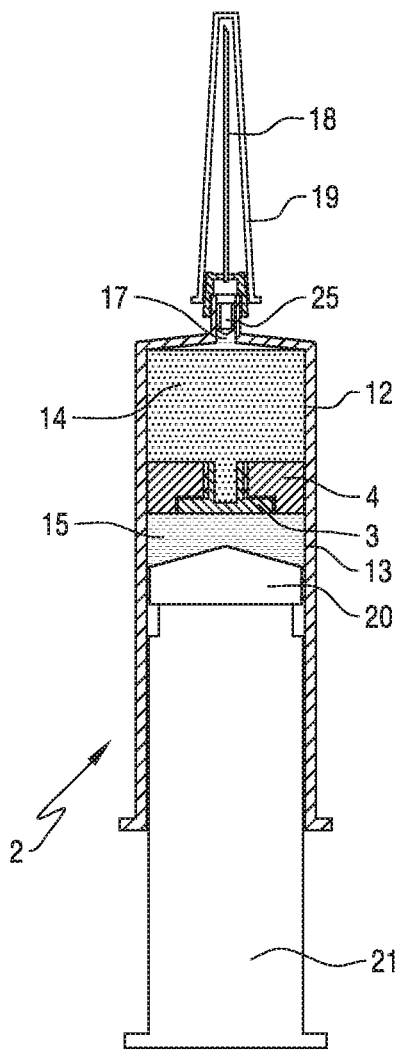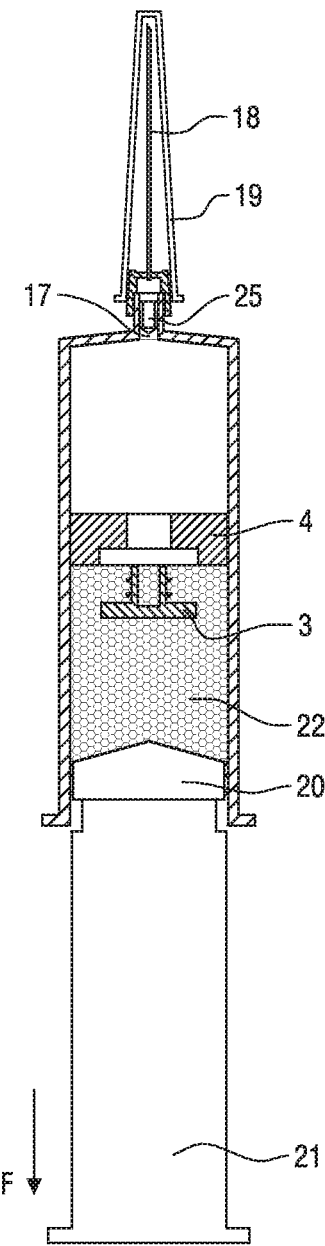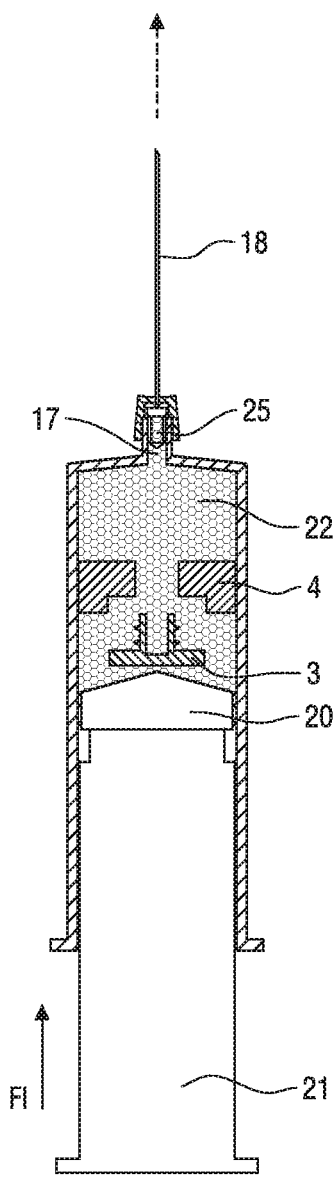
Fig. 19
Fig. 20
Fig. 21

US 11,027,074 B2

ELASTIC AND SLIDING VALVULAR JOINT, SUITABLE TO WORK IN PRE-FILLED SYRINGES AND SAID SYRINGES

FIELD OF THE INVENTION

The present invention makes reference to the field of syringes to apply injections, preferably to those pre-filled and disposable syringes, and even more particularly to an elastic and sliding valvular joint for pre-filled disposable syringes to maintain the contents therein completely isolated and sterile, preventing them to reach the needle before the injection.

BACKGROUND OF THE INVENTION

Generally, the pre-filled syringes include a cylindrical and hollow main body, with a front section where a communication neck is formed with the injection needle; while on the inside there is a plunger coaxially arranged and manually movable. This plunger extends outwards from the base opposite to the neck, which is totally open.

Under these conditions, an internal chamber of variable volume is defined. This chamber constitutes the temporary location for the product to be injected. Said chamber is determined by the cylindrical wall of the main body, the cited front neck, where the needle couples, and the active head of the plunger manually movable that is exactly supported by the internal face of said cylindrical wall of the main body.

The needle is housed in the interior of a protective sheath, which at the same time locks and couples to it keeping it isolated and steady, while it also couples to the syringe itself producing a temporary hermetic closure.

Taking into consideration the basic structure previously described, there are several embodiments where the mentioned interior of the main body is also subdivided in two chambers of variable volume that are adjacent and coaxial, and separated between them by internal transversal partitions, which include valvular means for the communication between both chambers.

It makes reference to the usually called pre-filled double-chamber syringes, which are used for those cases where two different liquid products are stored, or when one liquid product and another powdered product must be kept completely isolated and separated one from the other until the moment of injection, where they are previously mixed.

Indeed, in the case of double-chamber syringes, said internal valvular means, which constitute the partition that separates both chambers, are designed for the user to mix the products before the injection without being contaminated by the outer environment. That is to say, it maintains the isolation from origin. It is then that the protective sheath can be removed from the needle and, the resulting mix can be moved to the needle, initiating the injection process.

In order to carry out said mixing step, while maintaining the mentioned isolation, it is usual and common to use the plunger of the syringe itself moving it in a direction opposite to the direction of the injection. This moving action generates pressures and depressions in said adjacent chambers; and therefore, the mentioned internal valvular means open, establishing a communication that allows one of the products to pass and mix with the other, and then placing the mix in only one chamber and in the conditions to be injected.

Once the mix is made the same user shad only proceed with the injection for the mix to move forward towards the needle.

There are several constructive embodiments that define said internal valvular partitions, which separate the adjacent chambers that contain the separated products. Precisely, they differ by the valvular resource they include in each case.

However, from the analysis of these well-known internal valves, there arises the problem of the valvular means especially designed for each particular case. That is to say, they can only act in the body of a syringe that is structurally and functionally adapted to them.

In other cases, there are valvular elements that can be adapted to the body of conventional syringes, but which require the addition of an accessory or a structural modification to the body of the syringe, which raises theft final price and complicates their manufacture and filling.

It is further clarified that in order for these valvular joints to act effectively in pre-filled double-chamber syringes, it is important that the mentioned neck of the syringe, where the injection needle couples with its protective sheath, remains closed by a valve-plug or, otherwise by an adequate element that keeps the liquid isolated in the interior of the needle until the injection. In this manner, it guarantees that the coupling and uncoupling actions shall not cause an unwanted loss or spill.

Within this type of valvular joints, it is possible to find the Argentine Patent of Invention No AR 026723 B1. Its owners are Jaime Luis Szapiro, Saúl Moreno and Leonardo Szames and, it is entitled "ELASTIC AND SLIDING VALVULAR JOINT, SUITABLE TO WORK IN PRE-FILLED SYRINGES" ("CONJUNTO VALVULAR ELÁSTICO Y DESLIZANTE APTO PARA ACTUAR EN EL INTERIOR DE JERINGAS PRELLENADAS"). This invention belongs either to the internal single-chamber type, which stores the product to be injected, or to the internal and independent double-chamber type, which holds the corresponding isolated products that must be mixed before the injection. This valvular joint acts as a temporary closure that prevents said internal chambers from communicating between them or with the communication tube towards the injection needle.

The joint consists of two discoid cooperative elements arranged inside the main body of the syringe, where their perimeter edges are supported by the cylindrical surface of the body. One of said elements is an elastic and sliding discoid valve, while the other constitutes the sliding discoid seat on which said discoid valve acts. This discoid valve has an elastic base with multiple holes from where a stub is formed. This stub is opposite to a corresponding passage hole that is defined in the base of said sliding discoid seat.

The perimeter edges of the bases of both discoid cooperative elements determine thicker and less elastic cordons than the rest of the body of each valvular element.

According to this disclosure, the mentioned discoid cooperative elements, which are arranged above the internal communication between the main body and the neck of the syringe, may act as a resource of temporary closure for pre-filled single-chamber syringes; or if they are combined with a valvular plug that closes the neck of the syringe, they may act as a resource of temporary closure for pre-filled syringes with two internal coaxial chambers, acting as a separating partition between them.

It has been verified that in this type of disposable syringe, after mixing the product to be injected and moving the plunger of the syringe to perform the injection, the mentioned elastic and sliding discoid valve, which holds the closing stub of the passage that defines the sliding discoid seat, releases said passage. However, it tends to return to its closing position.

In effect, in some cases, when the user proceeds with the injection, he/she detects that the mentioned closing stub wrongfully enters the passage hole of the discoid seat, acting as an unexpected plug and generating the need of repeating the initial handling by moving the plunger backwards again and, hence releasing the passage again.

This happens due to the mentioned closing stub that keeps aligned with the referred passage hole. Although it has a diameter slightly bigger than said hole, it generates an undesired blockage when it settles due to the pressure produced by the plunger.

In this case it is sufficient to restart the filling action by moving the plunger of the syringe in an opposite direction to the direction of the injection in order for the stub to uncouple.

In this respect, the Argentine Patent of Invention AR 082099 A1, owned by Jaime Luis Szapiro, Saúl Moreno and Leonardo Szames, and entitled "ELASTIC AND SLIDING VALVULAR JOINT FOR DISPOSAL PRE-FILLED SYRINGES" ("CONJUNTO VALVULAR ELÁSTICO Y DESLIZANTE PARA JERINGAS PRELLENADAS DESCARTABLES"), makes reference to a valvular joint suitable to be used either in pre-filled syringes of a single internal chamber type that stores the product to be injected, or in those of two independent internal chambers that contain the corresponding isolated products to be mixed before the injection. This valvular joint acts as a temporary closure that prevents said internal chambers from communicating between them, or with the communication tube towards the injection needle. Said valvular joint consists of two cooperative discoid elements arranged inside the main body of the syringe, with their perimeter edges supported by its cylindrical surface. One of said elements is a sliding and elastic discoid plug, while the other consists of a sliding receiving discoid seat, on which said plug acts. The perimeter edges of the bases from both discoid elements determine each cordon, which are thicker and less elastic than the rest of the body of each valvular element.

The sliding and elastic discoid plug consists of an elastic base with multiple holes; and from its internal face a hollow closing cylinder with an open distant base is formed. Moreover, the sliding receiving discoid seat includes a central passage tube opposite to said dosing cylinder, which has superficial cavities in its internal opening that maintain the communication with the internal tube.

Additionally, the closing cylinder formed from the elastic base of the valvular plug has a circular section, which has an external diameter that is slightly bigger than the diameter of the passage tube of the receiving discoid seat.

Therefore, it is necessary to have a valvular joint with a simplified design that allows a more effective functioning and, instead of needing the manufacturing of the elements of the valvular joint only by injection of an elastomer, such as Santropene, (which is a thermoplastic rubber to be processed on plastics machinery but with the final appearance and features of rubber), it allows the use of different methods of manufacturing, such as the elastomer compression molding and other types of cheaper materials for medical use. This may be the case of butyl rubber, which is a synthetic copolymer rubber of isobutylene with isoprene ("IIR"- Isobutylene Isoprene Rubber, for its acronym in English), widely used in current pharmacotechnics.

Moreover, when the solution to be injected (for example, powder with a dissolved active in a suitable solvent) and resulting from the mixing process moves towards the upper chamber of a pre-filled syringe, or when the solution to be injected from a pre-filled syringe is in a single chamber, it is necessary to have a valvular joint that allows the free flow of the solution to be injected through a wide tube and not through small holes; so that consequently and with the upthrust of the plunger, the components of the valvular joint can act together and assemble with the plunger in the first case, or they can assemble again when finalizing the injection in the second case.

SUMMARY OF THE INVENTION

Therefore, the main object of this invention is a sliding and elastic valvular joint suitable to work in the interior of pre-filled syringes of a single-chamber type that stores the product to be injected, or in those of two independent internal chambers that contain the corresponding isolated products to be mixed before the injection. This valvular joint acts as a temporary closure that prevents an internal chamber from communicating with the communication tube towards the injection needle or between both internal chambers. Said valvular joint consists of two cooperative discoid elements arranged inside the main body of the syringe, with its perimeter edge supported by its cylindrical surface. One of said elements is an elastic discoid plug, while the other consists of a sliding receiving discoid seat, on which said plug acts through a cylindrical cavity. The perimeter edge of the discoid seat consists of a cordon, which is thicker and less elastic than the rest of the body of each discoid seat. The elastic discoid plug of said valvular joint consists of an elastic base and, from its internal face a closing hollow cylinder is formed with an open distant base. The sliding receiving discoid seat includes a central passage tube facing the dosing hollow cylinder, in such a way that the elastic base of the discoid plug fits in a removable manner inside a cylindrical cavity of the opening of the central passage tube of the sliding receiving discoid seat. The diameter of the elastic base of the elastic discoid plug is equivalent to the diameter of the sliding receiving discoid seat. When the hollow closing cylinder is inside the central passage tube of the sliding receiving discoid seat, said elastic base of the elastic discoid plug fits inside a circular cavity surrounded by the perimeter edge of the discoid seat that forms the thicker cordon, and where the external diameter of the hollow dosing cylinder is equivalent to the internal diameter of the central passage tube of the sliding receiving discoid seat offering a calibrated fit.

Alternatively, the closing hollow cylinder that is formed from the elastic base of the elastic discoid plug of the elastic valvular joint has a circular section, where the external diameter is slightly bigger than the diameter of the central passage tube of the sliding receiving discoid seat, offering a calibrated fit.

In another alternative way, the dosing hollow cylinder that is formed from the elastic base of the valvular plug of the elastic valvular joint includes a plurality of external annular flanges that are temporarily supported by the cylindrical surface defined by the central passage tube from the sliding receiving discoid seat, offering a calibrated fit.

Additionally, the central passage tube of the sliding receiving discoid seat of the elastic valvular joint includes in its opening at least two superficial adjacent cavities facing each other, which communicate with the interior of the central passage tube of the sliding receiving discoid seat.

Preferably, the cooperative discoid elements of the elastic valvular joint combined with an upper closure plug (tip-cap) that closes the communication tube towards the injection needle, which is not pre-installed in its position, act as a temporary closure for pre-filled syringes of two internal coaxial chambers, where said cooperative discoid elements are arranged as a separating partition between them.

It is also preferably that the cooperative discoid elements of the elastic valvular joint that are combined with a valvular plug that doses the communication tube towards the injection needle, which is pre-installed in its position, be a temporary closure for pre-filled syringes of two internal coaxial chambers, where said cooperative discoid elements are arranged as a separating partition between them.

In a preferred embodiment, the cooperative discoid elements of the elastic valvular joint, which are arranged as a temporary closure that prevents the internal communication of the main body of the syringe with the communication tube towards the injection needle, which may be pre-installed or not, act as a temporary closure for pre-filled single-chamber syringes.

In another embodiment, the present invention refers to a pre-filled syringe that consists of an elastic valvular joint according to any of the above claims, forming two cavities, where each one of them holds a different product being at least one of them liquid; and where both products after being mixed result in a solution to be injected, and the elastic discoid plug of the elastic valvular joint is opposite to the head of the plunger, Particularly, when the injection needle is pre-installed in the exit tube of the syringe, said tube is closed by an internal valvular closure plug.

In another embodiment, the present invention refers to a pre-filled syringe that consists of an elastic valvular joint according to any of the above claims, forming a cavity that includes a solution to be injected, where the elastic discoid plug of the elastic valvular joint is opposite to the head of the plunger.

Particularly, the injection needle is pre-installed in the exit tube of the syringe.

BRIEF DESCRIPTION OF THE DRAWINGS

Despite the advantages the users or specialists could add to this invention, aiming to specify the advantages cursory mentioned above, and in order to facilitate the understanding of the structural and functional characteristics of this invented elastic valvular joint, a preferred embodiment is described below and illustrated in a schematic manner and without a specific scale, in the sheets of drawings attached herewith. It is important to state dear that since it is a preferred embodiment, its scope of protection should not be considered limiting or exclusive. Instead, it is simply aimed to explain and illustrate the basic understanding upon which the invention is based.

FIG. 1 is a cross-section view that shows the separated elements that form the elastic valvular joint of this invention.

FIG. 2 is a cross section view, which is similar to the previous figure and, in this case shows the same elements coupled between them.

FIG. 3 is a perspective view that represents the elastic discoid valvular plug that constitutes one of the two elements from the invented valvular joint as seen from its external face.

FIG. 4 is a perspective view that represents the elastic discoid valvular plug that constitutes one of the two elements from the invented valvular joint as seen from its internal face.

FIG. 5 is a perspective view that represents the sliding receiving discoid seat that constitutes the other element from the invented valvular joint as seen from its external face.

FIG. 6 is a perspective view that represents the sliding receiving discoid seat that constitutes the other element from the invented valvular joint as seen from its internal face.

FIGS. 11, 12 and 13 are lengthwise cross-section views, which are similar to the previous figures, and in this case they gradually show the arrangement of the two valvular elements that belong to the invented joint when the resulting mix is moved to be placed in conditions suitable to be injected.

FIGS. 14 and 15 are lengthwise cross-section views, which are similar to the previous figures, and in this case they show the arrangement of the valvular elements that belong to the invented joint when injection is occurring.

FIG. 19 is a vertical lengthwise cross-section view that represents a double-chamber pre-filled syringe of conventional variable volume, in which interior the valvular joint of this invention is arranged at a rest position as provided in the commerce, with the injection needle previously installed in its protective sheath and the valvular closure plug that prevents the product to be injected and inside the syringe from communicating with the injection needle.

FIG. 20 is a vertical lengthwise cross-section view that represents a double-chamber pre-filled syringe of conventional variable volume from FIG. 18, in which interior the valvular joint of this invention acts allowing the mix of the products arranged in separate chambers, and there being an injection needle previously installed in its protective sheath, and a valvular closure plug preventing the product to be injected and inside the syringe from communicating with the injection needle.

FIG. 21 is a vertical lengthwise cross-section view that represents a double-chamber pre-filled syringe of conventional variable volume from FIG. 18, showing the performance of the elements of the valvular joint of this invention when the product of the pre-filled syringe is moved during the injection process towards the pre-installed injection needle without its protective sheath, and where the valvular-closing plug allows the communication of the product inside the syringe with the injection needle.

It is further clarified that in all the figures the same reference numbers correspond to the same or equivalent parts or elements forming the joint, according to the embodiment selected for this explanation of the invented valvular joint.

DETAILED DESCRIPTION OF THE INVENTION

Figures 7, 8, 9, 10:
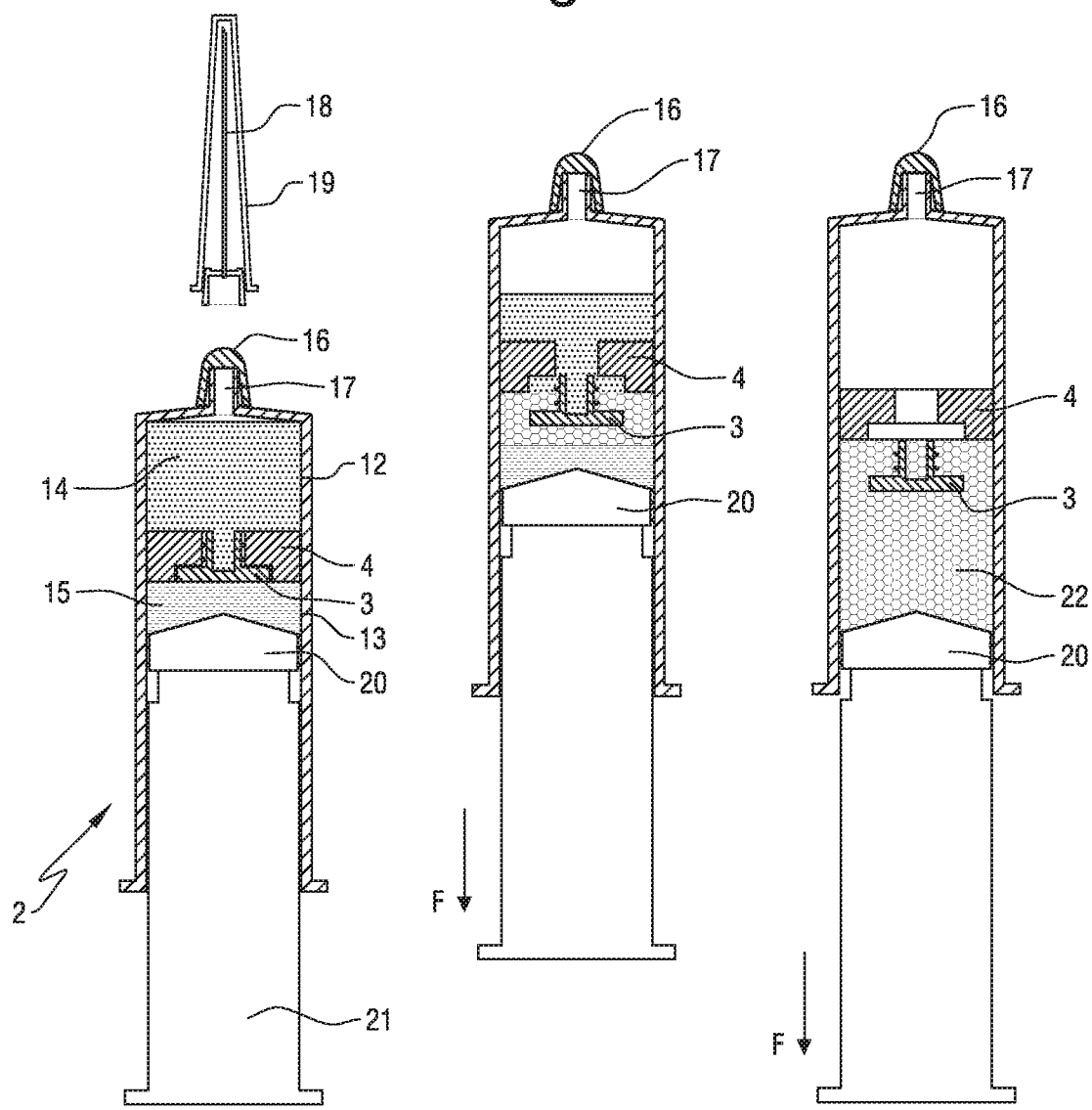
FIG. 7 is a perspective view that represents the other preferred embodiment of a sliding receiving discoid seat that constitutes the other element from the invented valvular joint, as seen from its internal face, where two opposite tubes can be seen in the opening of the cylindrical tube.
FIG. 8 is a vertical lengthwise cross-section view that represents a pre-filled double-chamber syringe of conventional variable volume, in which interior the valvular joint of this invention is arranged at a rest position as it is offered in the commerce.
FIG. 9 is also a lengthwise cross-section view, which is similar to the previous figure, and in this case it shows the invented valvular joint in the position after the mixing process is initiated inside the syringe.
FIG. 10 is also a lengthwise cross-section view, which is similar to the previous figures, and in this case it shows the invented valvular joint in the position after the mixing process is finished inside the syringe.

The valvular joint of this invention belongs to the group of those adaptable to any type of body of the conventional syringe, whether single-chamber or double-chamber.

The constructive and functional design of this valvular joint takes into account the condition of adapting to any type of conventional syringe, the non-alteration of automatized processes for getting the products inside the syringe, especially for the cases of double-chamber pre-filled syringes, and also the lack of special and/or complicated tasks demanded to the user when mixing and later injecting.

As it is noticed in FIGS. 1 to 7, the elastic and sliding valvular joint (1) for syringes (2) previously filled and referred to in this invention consists of two mutually cooperative elements represented by (3 and 4).

The one indicated with reference (3) is an elastic discoid plug that consists of an elastic discoid base (5) substantially formed in a cylindrical manner.

This elastic discoid plug (3) stands out especially since a dosing hollow cylinder (6), which is coaxial with the mentioned elastic discoid base, is formed from its internal face and, its distant face is totally open.

The second element, a receiving discoid seat (4), has been created to allow the elastic discoid plug (3) to produce the closure or opening of the valvular joint (1), acting as a cooperative receiving discoid seat. This element is also preferably circular and it includes a central passage tube (7) and its corresponding perimeter ring (8) that is thicker than the rest of the body of said element.

As an alternative embodiment to the invention, this sliding receiving seat (4) is characterized especially due to the opening of its central passage tube (7), which is opposite to the dosing hollow cylinder (6) of the elastic discoid plug (3) from the valvular joint (1). Furthermore, it preferably includes at least two superficial adjacent cavities (9 and 10) of short length, and each one of them constitutes a channel that communicates with the mentioned central passage tube (7).

The elastic discoid plug (3) and the receiving discoid seat (4) of the valvular joint (1) are cooperative elements because they must necessarily act together for the valvular opening and dosing actions.

To this extent, said elements (3 and 4) must be overlapped and aligned between them inside the syringe; so that the mentioned dosing cylinder (6) perfectly fits the interior of the central passage tube (7) generating the hermetic closure that prevents the products contained inside the syringe (2) previously filled from moving through said tube.

Said proper fit in the interior of the central passage tube (7) is obtained through a bigger diameter of the closing hollow cylinder (6).

As an alternative embodiment, said bigger diameter of the closing hollow cylinder (6) can be obtained through a plurality of external annular flanges (11), which are temporary supported by the cylindrical surface that defines the central passage tube (7) of the sliding receiving discoid seat (4).

As an alternative to this invention, in case the closing hollow cylinder (6) of the elastic discoid plug (3) is arranged to be supported by the central passage tube (7) of the receiving discoid seat (4), at least two of the mentioned superficial cavities (9 and 10) guarantee the flow of the fluid towards the exit of the syringe (2) during the injection without drawbacks.

As from FIGS. 8 to 13, it is possible to understand how the invented joint acts when it is applied to a syringe (2) previously filled with two chambers (12 and 13) during the process of mixing of products (14 and 15) contained in both chambers (12 and 13).

Indeed, in FIG. 8 it is possible to observe, in a lengthwise cross-section view, a syringe (2), which is conventional and pre-filled as it is before the injection conditions, i.e. with the corresponding products (14 and 15) duly separated and isolated between them and with the exterior and stored in the respective chambers (12 and 13) of variable volume inside the body of the syringe (2).

By means of an upper closure plug (16), also known as "tip-cap", which is in the exit tube (17) of the syringe (2), it is possible to guarantee the airtightness and hence, the duly isolation of the commercial product.

As it is already known, the syringe (2) includes its corresponding needle (18) of injection, which is covered by a protective sheath (19), which usually accompanies the commercial product in its container.

In said FIG. 8 it can be clearly identified that the upper chamber (12) of the syringe (2), which is closer to the exit of the product during the injection, is delimited in its base by the valvular joint (1) of the invention, in its sides by the internal face of the cylindrical wall of the main body of the syringe (2) and in the upper part by the mentioned closure plug (16), containing the first product (14) duly isolated.

Furthermore, the lower chamber (13) is delimited in its upper part by the same valvular joint (1), by the internal face of the cylindrical wall of the main body of the syringe (2) and by the head (20) of the plunger (21), containing the second product (15) duly isolated.

In the conditions mentioned above, as it is shown in FIG. 8, it is possible to store in said chambers (12 and 13) two products, the first one (14) and the second one (15), which may be liquid or solid in powder-form; preferably, for example one liquid and one solid in powder-form, or two liquids. In both cases they are separately contained in any of the two chambers (12 and 13).

Once the joint is initially formed, while observing said FIGS. 9 to 13 it is possible to notice the performance of the valvular joint (1) in this invention when the internal mixing action of the products (14 and 15) begins before the injection.

For this purpose the user moves the head (20) of the plunger (21) in the direction (F) opposite to the direction of the injection, generating a depression in the lower chamber (13), which consequently produces the movement of the elastic discoid plug (3) liberating the central passage tube (7) of the receiving discoid seat (4), and hence liberating the communication between both upper and lower chambers (12 and 13). This is possible because when said movement occurs, the product (14) flows through the central tube (7) of the receiving discoid seat (4).

In order to facilitate the obtaining of the solution (22) of the injection, it is preferably that the user vigorously shakes the syringe (2).

FIG. 13 shows the arrangement of the referred elements (3 and 4) and the obtaining of the solution (22) to be injected by mixing the referred products (14 and 15), which is completely located in the upper distant chamber (12) and which is always duly isolated from the exterior by a closure plug (16).

It is emphasized the fact that the elastic discoid plug (3) is kept out of its position with respect to the central passage tube (7) of the receiving discoid seat (4), and the communication is kept between both internal chambers (12 and 13) during the actions to obtain the solution (22) to be injected.

FIGS. 11, 12 and 13 show that as a consequence of the communication set through the central passage tube (7), when the user moves the head (20) of the plunger (21) in the direction (Fl) of the injection, the mentioned solution (22) moves from the lower or closer chamber (13) towards the upper or distant chamber (13) in a way that the solution is possible to be injected (22). Said solution was obtained in the same was as any other prefilled syringe (2) of a single conventional chamber.

The pressure made from the plunger (21) makes the closing hollow cylinder (6) of the elastic discoid plug (3) to settle on the opening of the central passage tube (7) and to fit it, which is why the valvular joint (1) works together during the injection of the content of the syringe (2), and in which case it does not affect the flow of fluid. This occurs because the fluid flowed perfectly and completely since said elastic discoid plug (3) did not completely close the tube (7).

In this respect the closing hollow cylinder (6) has the same diameter or a bigger diameter than the central tube (7), which prevents the communication between the chambers (12 and 13) from dosing until the direct pressure from the plunger (21) obliges the plug to returns to its initial position.

Notwithstanding the above, and as an alternative embodiment, the valvular joint (1) of this invention includes superficial cavities (9 and 10) adjacent to the opening of communication of the cited passage tube (7). So, in case said dosing hollow cylinder (6) is supported by the opening of the passage tube (7), the solution fluid (22) normally flows through the mentioned cavities (9 and 10).

FIGS. 14 and 15 show that once the upper closure plug (16) is withdrawn and the injection needle (18) is placed in its position in the distant end of the exit tube (17) of the syringe (2), it will be sufficient for the user to continue moving the plunger (1) in the direction (Fl) such that the pressure applied to the solution itself (22) makes it flow through the needle (19) of the injection by crossing it, after having previously removed the protective sheath (19) from said needle (18).

Figure 16:
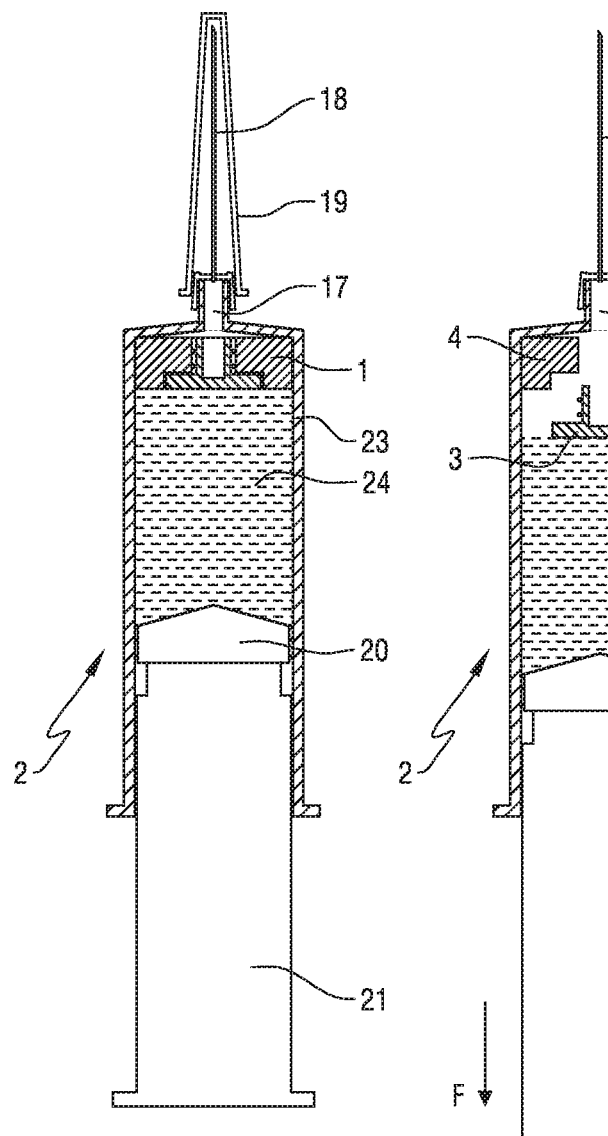
FIG. 16 is a lengthwise cross-section view that shows the simple-chamber syringe of conventional variable volume, where the invented valvular joint is also included. However, in this case, the joint acts as a seal that prevents the content of the syringe from entering the needle channel.
Figure 17:
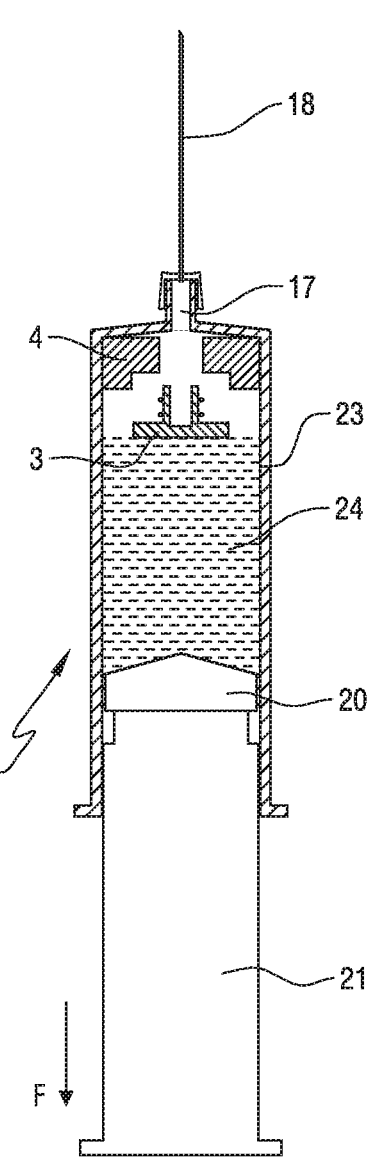
FIG. 17 is a lengthwise cross-section view similar to the previous FIG. 16, which shows the performance of the valvular elements when applying F force with the plunger outside the pre-filled syringe and moving the plug of the valvular joint before the injection process.
Figure 18:
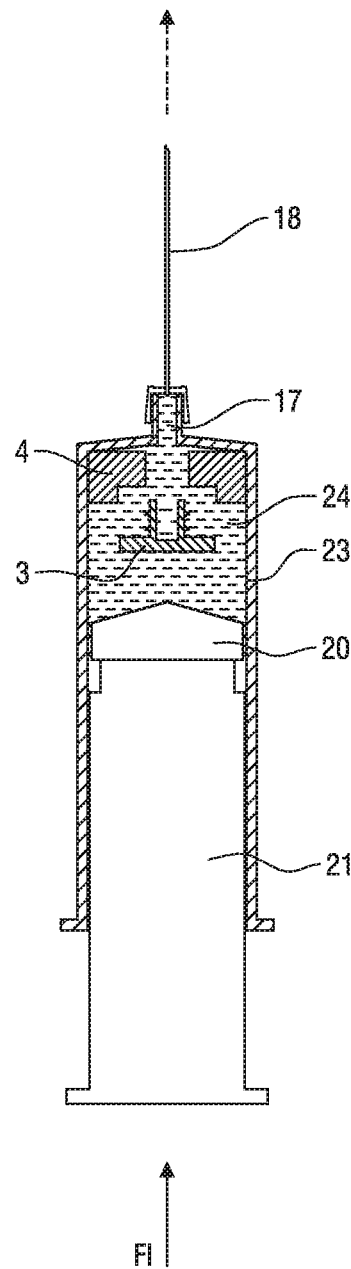
FIG. 18 is a lengthwise cross-section view similar to the previous FIG. 16, which shows the performance of the valvular elements when the product of the pre-filled syringe is moved through the syringe and the needle during the injection process.

FIGS. 16, 17 and 18 show the valvular joint (1) according to this invention included in a pre-filled conventional syringe (2) of only one chamber (23).

Indeed, for these cases the valvular joint (1) formed by elements (3 and 4) is placed in a way that it closes the internal communication of the syringe (2) with the exit tube (17) of the syringe (2), in such a manner that only the chamber (23) is delimited by the valvular joint (1) as the upper base, and by the cylindrical wall of the main body of the syringe (2) and the head (20) of the plunger (21) as the lower base.

In this case, the user also moves the plunger (21) in the inverse direction (F) of the injection producing an internal depression that generates the elastic deformation of the elastic discoid plug (3), and hence the movement of the closing hollow cylinder (6), which opens a communication through the central passage tube (7). Moreover, when applying an inverse force (Fl), the injectable stored solution (24) can exit towards the needle (18) of the injection, and cross it after having previously removed the protective sheath (19) from said needle (18).

In both cases mentioned above, whether the pre-filled syringe (2) of two chambers (12 and 13) or of a single chamber (23), the internal communication of the syringe (2) through the exit tube (17) is initially and necessarily blocked by an upper closure plug (16) or "tip-cap", which is located in the exit tube (17) of the syringe (2), while the needle (18) of the injection is inside the protective sheath (19) and separated from the syringe (2) inside its corresponding packaging.

In the market there are syringes (2) previously filled, which are commercialized with the needle (18) being previously installed in their exit tube (17). Said syringes (2) may have two chambers (12 and 13) or one chamber (23) to contain two separate products that are mixed to obtain either one solution (22) to be injected or one injectable solution (24), respectively.

In the first case, the valvular joint (1) according to this invention may be used to separate both internal chambers (12 and 13), while the distant chamber (12) of the exit tube (17) of the syringe (2) of the needle (18) is separated by using the valvular closure plug (25) as it is described in the invention patent from Argentina 250777 V1, owned by Jaime Luis Szapiro, Leonardo Szames and Saúl Moreno, and entitled "VALVULAR SAFETY PLUG APPLICABLE TO DISPOSABLE PRE-FILLED SYRINGES" ("TAPÓN VÁLVULA DE SEGURIDAD APLICABLE A JERINGAS PRELLENADAS DESCARTABLES"), and the contents and studies of which are included herein by reference in their entirety.

In this way, in those cases, where it is required to have a needle (18) of injection on top of the distant exit tube (17) of the syringe (2) previously filled, and when the valvular joint (1) of this invention must separate two chambers (12 and 13) with different products (14 and 15) to be mixed with the aim to obtain an injectable solution (22), said exit tube (17) must include a block, which may occur by means of a valvular closure plug (25) acting in the interior of the exit tube (17) of the syringe (2), where the injection needle (18) is already installed. Due to its special formation, said valvular closure plug (25) allows the exit of the solution (22) to be injected only when a force (Fl) is applied producing an hydraulic pressure from the plunger (21) towards the syringe (2), which partially moves the valvular closure plug (25) and allows the flow of the solution (22) to be injected.

However, it is important to highlight that according to this invention, the aim and function of this dosing valvular plug (25) does not affect the aim and function of the valvular joint (1). Instead, it is an alternative to the making of syringes (2) previously filled and of two chambers (12 and 13) that are separated by the valvular joint (1) according to this invention.

In FIG. 19 it is possible to see a syringe (2) previously filled and of two chambers (12 and 13) with its corresponding needle (18) of injection previously installed and covered by its protective sheath (19), which is duly coupled to the exit tube (17) of the syringe (2) previously defined.

In FIG. 20 it is possible to see an internal communication between the chambers (12 and 13), where said internal upper closing valvular plug (25) also acts guaranteeing the hermetic closure and hence, the duly isolation of the solution (2) to be injected.

As it can be seen in FIG. 21, the closing valvular plug (25) is particularly characterized by the fact that it partially moves outwards allowing the exit of the solution (22) to be injected, and which was obtained from the mixing of products (14 and 15), through the needle (18). This movement occurs when internal pressure is generated during the action of injection by applying force (Fl) on the plunger (21).

After describing and illustrating the nature and main object of the invention, as well as the way in which it can be put into practice, the following is claimed as exclusive rights and ownership:

1. A pre-filled syringe having:
   (a) one internal chamber that stores a product to be injected, or
   (b) two internal independent chambers that contain isolated products, respectively, and which have to be mixed before injection,
   (c) an elastic and sliding valvular joint disposed inside a main body of said pre-filled syringe and configured and arranged to form a temporary closure blocking communication between (a) the one internal chamber and a communication channel towards an injection needle, or (b) between the two internal chambers, said elastic and sliding valvular joint comprising:
   first and second discoid cooperative elements, wherein the first of the discoid cooperative elements comprises a perimeter having an edge supported by an internal cylindrical surface of the syringe, wherein the second of said discoid cooperative elements is an elastic discoid plug, the first of said discoid cooperative elements forming a sliding discoid receiving seat comprising a central passage tube for receiving said elastic discoid plug, wherein the perimeter edge of the discoid receiving seat forms a rim that is thicker and less elastic than the rest of said discoid receiving seat,
   wherein the elastic discoid plug comprises an elastic base and a hollow closing cylinder with an open distal base formed from an internal face of the elastic base, the hollow closing cylinder optionally comprising a plurality of external flanges supported on a cylindrical surface thereof,
   wherein the central passage tube of the sliding discoid receiving seat faces said hollow closing cylinder and comprises an upper cylindrical cavity disposed in an opening of the central passage tube and a lower cylindrical cavity in communication with the upper cylindrical cavity, the central passage tube being configured so that the elastic discoid plug fits in a removable manner inside the central passage tube with the hollow closing cylinder of the discoid plug disposed in the lower cylindrical cavity and the elastic base of the discoid plug disposed in the upper cylindrical cavity surrounded by the perimeter edge of the discoid seat that forms the thicker rim,
   wherein, if the hollow closing cylinder does not comprise the plurality of external flanges, an outer diameter of the hollow closing cylinder of the elastic discoid plug is the same size as or is slightly bigger than an internal diameter of the lower cylindrical cavity and, if the hollow closing cylinder comprises the plurality of external flanges, the outer diameter of the hollow closing cylinder is dimensioned such that, with the hollow closing cylinder of the discoid plug disposed in the lower cylindrical cavity, the plurality of external annular flanges are supported by a cylindrical surface on the central passage tube of the sliding discoid receiving seat; and
   wherein the discoid cooperative elements of the elastic and sliding valvular joint are formable from an elastomeric material configured to be formed by either an injection process or by a compression process.

2. The pre-filled syringe according to claim 1, wherein the outer diameter of the closing cylinder is slightly bigger than the diameter of the central passage tube of the sliding receiving discoid seat.

3. The pre-filled syringe according to claim 1, wherein the hollow closing cylinder formed from the elastic base of the elastic discoid plug comprises the plurality of external annular flanges.

4. The pre-filled syringe according to claim 1, wherein the central passage tube of the sliding discoid receiving seat comprises at least two superficial adjacent cavities in the opening, which are opposed to each other and which communicate with the upper cylindrical cavity of the sliding receiving discoid seat.

5. The pre-filled syringe according to claim 1, wherein the pre-filled syringe comprises the two internal independent chambers that contain the isolated products, wherein said discoid cooperative elements are arranged to act as a separating partition between the two internal independent chambers that contain the isolated products and wherein the pre-filled syringe also comprises an upper closure plug for closing a communication channel between the two internal independent chambers and the injection needle.

6. The pre-filled syringe according to claim 5, wherein the upper closure plug is a tip-cap plug.

7. The pre-filled syringe according to claim 1, the pre-filled syringe comprises the two internal independent chambers that contain the isolated products, wherein said discoid cooperative elements are configured to act as a separating partition between the two internal independent chambers that contain the isolated products, and wherein the pre-filled syringe also comprises a valvular closure plug for closing a communication channel between the two internal independent chambers and the injection needle.

8. The pre-filled syringe according to claim 1, wherein the pre-filled syringe comprises the one internal chamber that stores the product to be injected and the discoid cooperative elements are arranged as a temporary closure to prevent the main body of the syringe from communicating internally with the communication channel towards the injection needle.

9. The pre-filled syringe according to claim 1, wherein the pre-filled syringe comprises the two internal independent chambers that contain the respective isolated products, wherein at least one of the isolated products is liquid, wherein upon mixing the products, an injectable solution is obtained, and wherein the pre-filled syringe comprises a plunger and the elastic discoid plug of the elastic and sliding valvular joint faces a head of the plunger.

10. The pre-filled syringe according to claim 9, wherein the injection needle is pre-installed in the communication channel of the syringe said communication channel is closed by an internal valvular closure plug.

11. The pre-filled syringe according to claim 1, wherein the pre-filled syringe comprises the one internal chamber that contains the product to be injected, wherein the product is a solution and wherein the pre-filled syringe comprises a plunger and the elastic discoid plug of the elastic and sliding valvular joint faces a head of the plunger.

12. The pre-filled syringe according to claim 11, wherein the injection needle is pre-installed in the communication channel of the syringe.

13. A valvular joint for a syringe, comprising
   a) a plug comprising (i) a solid base portion having a shape of a cylindrical segment, (ii) a dosing portion projecting from a center of a bottom surface of the solid base portion, the dosing portion having a shape of a circular cylinder, the dosing portion being hollow and comprising an open end and, optionally, (iii) a plurality of annular flanges disposed on an external surface of the dosing portion, the plug being of unitary construction, the base portion having a radius that is greater than a radius of the dosing portion;

b) a seat for the plug having a side surface with a shape of a cylindrical segment, a top surface with a shape of an annulus and a bottom surface with a shape of an annulus, the annulus of the top surface having an opening that is larger than an opening of the bottom surface, the seat comprising an interior that defines i) the opening of the top surface into which the solid base portion of the plug seats with a top surface of the solid base portion even with the top surface of the seat, (ii) the opening of the bottom surface in a central portion of the seat communicating with the opening in the top surface and sized for receiving the dosing portion of the plug, and optionally iii) a plurality of cavities adjacent an area where the opening in the top surface and the opening in the bottom surface meet; the seat being of unitary construction and being made of an elastic material; the elastic material of the side surface being thicker and less elastic than a remainder of the seat;

wherein an outer diameter of the dosing portion of the plug is at least as large as an internal diameter of the cylindrical opening defined by the seat so as to prevent fluid from passing through the cylindrical opening of the seat with the dosing portion of the plug received in the cylindrical opening or wherein the plug comprises the plurality of annular flanges disposed on the external surface of the dosing portion and the dosing portion and the annular flanges are configured to prevent fluid from passing through the cylindrical opening of the seat with the dosing portion and the annular flanges received in the cylindrical opening.

14. The valvular joint according to claim 13, wherein the seat comprises the plurality of cavities.

15. The valvular joint according to claim 13, wherein the plug comprises the plurality of annular flanges.

16. The valvular joint according to claim 13, which consists of the plug and the seat.

17. A syringe pre-filled with first and second components of a medicament, the syringe comprising i) a body having a cylindrical wall;
ii) a medicament outlet;
iii) a plunger reciprocally movable within the cylindrical body in a first direction toward the medicament outlet and a second direction away from the medicament outlet; and
iv) the valvular joint according to claim 13, wherein the valvular joint is disposed within the body of the syringe with the seat in sealing connection with and slidable along the cylindrical wall such that the valvular joint can be moved toward the medicament outlet by movement of the plunger in the first direction and such that the valvular joint divides the cylindrical body into two chambers of variable volume, including a lower variable volume chamber proximal to the medicament outlet comprising the first component of the medicament and an upper variable volume chamber distal to the medicament outlet comprising the second component of the medicament; and wherein the plug is movable from a sealing position wherein it is seated in the seat to an open position spaced from the seat by a decrease of pressure caused by movement of the plunger in the second direction and the plug is movable from the open position to the sealing position by movement of the plunger in the first direction.

18. A syringe pre-filled with a medicament, the syringe comprising i) a body having a cylindrical wall;
ii) a medicament outlet;
iii) a plunger reciprocally movable within the cylindrical body in a first direction toward the medicament outlet and a second direction away from the medicament outlet; and
iv) the valvular joint according to claim 13, wherein the valvular joint is disposed within the body of the syringe with the seat in sealing connection with and slidable along the cylindrical wall such that the valvular joint can be moved toward the medicament outlet by movement of the plunger in the first direction; and wherein the plug is movable from a sealing position wherein it is seated in the seat to an open position spaced from the seat by a decrease of pressure caused by movement of the plunger in the second direction and the plug is movable from the open position to the sealing position by movement of the plunger in the first direction.

* * * * *